United States Patent
Kim et al.

(10) Patent No.: US 9,851,635 B2
(45) Date of Patent: Dec. 26, 2017

(54) PHOTORESIST COMPOSITION AND METHOD OF MANUFACTURING SUBSTRATE FOR DISPLAY DEVICE BY USING THE SAME

(71) Applicants: SAMSUNG DISPLAY CO., LTD., Yongin, Gyeonggi-Do (KR); AZ ELECTRONIC MATERIALS (LUXEMBOURG) SARL, Luxembourg (LU)

(72) Inventors: Chadong Kim, Yongin (KR); Hoon Kang, Yongin (KR); Wooyong Sung, Yongin (KR); Hikuk Lee, Yongin (KR); Changhoon Kim, Yongin (KR); Jungin Park, Yongin (KR); Sanghyun Yun, Yongin (KR); Kibeom Lee, Yongin (KR); Jaehyuk Chang, Yongin (KR); Deokman Kang, Anseong-si (KR); Younsuk Kim, Anseong-si (KR); Saetae Oh, Anseong-si (KR)

(73) Assignees: SAMSUNG DISPLAY CO., LTD., Yongin, Gyeonggi-Do (KR); AZ ELECTRONIC MATERIALS (LUXEMBOURG) SARL, Luxembourg (LU)

( * ) Notice: Subject to any disclaimer, the term of this patent is extended or adjusted under 35 U.S.C. 154(b) by 0 days.

(21) Appl. No.: 14/801,111

(22) Filed: Jul. 16, 2015

(65) Prior Publication Data
US 2016/0018731 A1 Jan. 21, 2016

(30) Foreign Application Priority Data
Jul. 16, 2014 (KR) ........................ 10-2014-0089800

(51) Int. Cl.
G03F 7/004 (2006.01)
G03F 7/20 (2006.01)
(Continued)

(52) U.S. Cl.
CPC ........... *G03F 7/004* (2013.01); *C07D 213/02* (2013.01); *G03F 7/0007* (2013.01);
(Continued)

(58) Field of Classification Search
CPC .... G03F 7/0045; G03F 7/0382; G03F 7/0384; C07D 213/02
(Continued)

(56) References Cited

U.S. PATENT DOCUMENTS 5,057,397 A * 10/1991 Miyabe ................ C08K 5/3492
430/270.1
5,180,653 A * 1/1993 Miyabe ................ C08K 5/3492
430/296
(Continued)

FOREIGN PATENT DOCUMENTS

JP 62212401 A * 9/1987
JP 07028243 A * 1/1995
(Continued)

*Primary Examiner* — Amanda C Walke
(74) *Attorney, Agent, or Firm* — F. Chau & Associates, LLC

(57) ABSTRACT

A photoresist composition includes an alkali soluble resin, a hardening agent, a photo acid generator, and an organic solvent. The photo acid generator may be represented by Formula 1, (Continued)

COMPARATIVE EXAMPLE 1

EXAMPLE 1

COMPARATIVE EXAMPLE 2

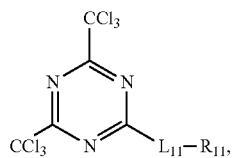

in which $L_{11}$ is selected from a single bond, a $C_1$-$C_{10}$ alkylene group, a $C_2$-$C_{10}$ alkenylene group, and a $C_2$-$C_{10}$ alkynylene group; and $R_{11}$ is selected from a $C_6$-$C_{15}$ aryl group, or a $C_6$-$C_{15}$ aryl group with at least one substitutent group selected from a group comprising deuterium, a hydroxyl group, a $C_1$-$C_{10}$ alkyl group, a $C_1$-$C_{10}$ alkoxy group, and a $C_6$-$C_{15}$ aryl group.

16 Claims, 9 Drawing Sheets

(51) Int. Cl.
| | | |
|---|---|---|
| *G03F 7/40* | (2006.01) | |
| *G03F 7/038* | (2006.01) | |
| *C07D 213/02* | (2006.01) | |
| *G03F 7/00* | (2006.01) | |
| *H01L 21/00* | (2006.01) | |

(52) U.S. Cl.
CPC ............ *G03F 7/0045* (2013.01); *G03F 7/038* (2013.01); *G03F 7/0382* (2013.01); *G03F 7/0384* (2013.01); *G03F 7/20* (2013.01); *G03F 7/2057* (2013.01); *G03F 7/40* (2013.01); *H01L 21/00* (2013.01)

(58) Field of Classification Search
USPC .............. 430/270.1, 905, 913, 927; 259/113; 251/2, 12
See application file for complete search history.

(56) References Cited

U.S. PATENT DOCUMENTS

| | | | | |
|---|---|---|---|---|
| 5,541,036 | A | * | 7/1996 | Igawa ..................... G03F 7/038 430/270.1 |
| 5,663,037 | A | * | 9/1997 | Haley ..................... G03F 7/038 430/157 |
| 5,719,008 | A | * | 2/1998 | Hozumi .................. G03F 7/027 430/281.1 |
| 5,731,125 | A | * | 3/1998 | Yamachika ............. G03F 7/091 430/270.1 |
| 7,098,993 | B2 | | 8/2006 | Fujii et al. |
| 7,811,726 | B2 | | 10/2010 | Kwon et al. |
| 8,795,943 | B2 | * | 8/2014 | Park ....................... G03F 7/0045 430/270.1 |
| 8,968,983 | B2 | | 3/2015 | Kim et al. |
| 2002/0055059 | A1 | * | 5/2002 | Nishimura ............ G03F 7/0045 430/270.1 |
| 2007/0117045 | A1 | * | 5/2007 | Maruyama ............ G03F 7/0392 430/270.1 |
| 2010/0009482 | A1 | | 1/2010 | Park et al. |
| 2011/0121435 | A1 | | 5/2011 | Mitsukura et al. |
| 2016/0177020 | A1 | * | 6/2016 | Imada ..................... C08G 8/28 430/270.1 |

FOREIGN PATENT DOCUMENTS

| | | |
|---|---|---|
| JP | 09-090633 | 4/1997 |
| JP | 2007-272138 | 10/2007 |
| JP | 2008-217036 | 9/2008 |
| KR | 1020070066445 | 6/2007 |

* cited by examiner

FIG. 2

| PATTERN SIZE | 3um | 2.4um | 2.2um | 2.0um | 1.8um | 1.6um |
|---|---|---|---|---|---|---|
| COMPARATIVE EXAMPLE 1 | 2.99 um | | | | | |
| EXAMPLE 1 | 3.27 um | 2.62 um | 2.32 um | 2.09 um | 1.76 um | 1.24 um |
| COMPARATIVE EXAMPLE 2 | 3.76 um | | | | | |

PHOTORESIST COMPOSITION AND METHOD OF MANUFACTURING SUBSTRATE FOR DISPLAY DEVICE BY USING THE SAME

CROSS REFERENCE TO RELATED APPLICATION

This application claims priority under 35 U.S.C. §119 from Korean Patent Application No. 10-2014-0089800, filed on Jul. 16, 2014 in the Korean Intellectual Property Office, and all the benefits accruing therefrom, the contents of which are herein incorporated by reference in their entirety.

BACKGROUND

1. Technical Field

One or more embodiments are directed to a photoresist composition and a method of manufacturing a substrate for a display device by using the same.

2. Discussion of the Related Art

Display substrates that include a thin film transistor (TFT) are formed using a photolithography process. A photolithography process includes an exposure process, a development process, and an etch process. In the exposure process, a photolithography pattern is formed by using a mask that corresponds to a pattern to be formed, and an exposure device, hereinafter called a general exposure device. A photolithography pattern is used as an etch prevention film to pattern a film disposed under the photolithography pattern, thereby forming a target pattern. Whenever a different pattern is used, a mask corresponding to that pattern is needed. Accordingly, a number of masks corresponds to the number of patterns. Since masks are high-priced, the use of the masks in a photolithography process leads to higher manufacturing costs. However, these costs may be reduced by using a digital exposure device that includes micromirrors that can provide a plurality of spot beams to a substrate without the use of separate masks.

However, a digital exposure device use a light source that generates light having a different wavelength than that of the general exposure device. Accordingly, when a photoresist composition having a high photosensitivity with respect to the general exposure device is used in a photolithography process, the photosensitivity of the photoresist composition with respect to the digital exposure device may decrease.

SUMMARY

One or more embodiments can provide a photoresist composition and a method of manufacturing a substrate for a display device by using the same.

An embodiment of the inventive concept provides a photoresist composition that includes an alkali soluble resin; a hardening agent; a photo acid generator represented by Formula 1; and an organic solvent:

<Formula 1>

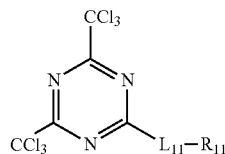

wherein in Formula 1, $L_{11}$ is selected from a single bond, a $C_1$-$C_{10}$ alkylene group, a $C_2$-$C_{10}$ alkenylene group, and a $C_2$-$C_{10}$ alkynylene group; and $R_{11}$ is selected from a $C_6$-$C_{15}$ aryl group, or a $C_6$-$C_{15}$ aryl group with at least one substitution selected from a group comprising deuterium, a hydroxyl group, a $C_1$-$C_{10}$ alkyl group, a $C_1$-$C_{10}$ alkoxy group, and a $C_6$-$C_{15}$ aryl group.

In some embodiments, the alkali soluble resin may include at least one selected from an acryl copolymer and a novolac-based resin.

In some embodiments, the novolac-based resin may include a mixture of 75 wt. % of meta-cresol and 25 wt. % of para-cresol.

In some embodiments, the novolac-based resin may have a weight average molecular weight of about 7,000 to about 30,000, based on polystyrene.

In some embodiments, the hardening agent may include at least one selected from an epoxy-based resin, a polyglycidylether-based resin, a diphenyl ether-based resin, a styrene resin, and a melamine-based resin.

In some embodiments, the melamine-based resin may include at least one selected from an alkoxymethylated melamine resin, an ethoxymethylated melamine resin, a propoxymethylated melamine resin, a butoxy methylated melamine resin, a hexamethoxymethylmelamine resin, a hexaethoxymethylmelamine resin, a hexabutoxymethylmelamine resin, and a hexaisobutoxymethylmelamine resin.

In some embodiments, $L_{11}$ may be selected from a single bond and a $C_2$-$C_{10}$ alkenylene group.

In some embodiments, $L_{11}$ may be selected from a single bond and an ethenylene group.

In some embodiments, $R_{11}$ may be selected from a phenyl group; or a phenyl group with at least one substituent group selected from a methyl group, an ethyl group, an n-propyl group, an iso-propyl group, a methoxy group, an ethoxy group, and a phenyl group.

In some embodiments, $R_{11}$ may be a phenyl group with a methoxy group.

In some embodiments, $R_{11}$ may be selected from Formulae 2-1 or 2-2:

2-1

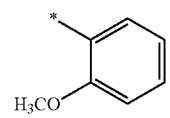

2-2

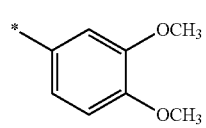

wherein * in Formulae 2-1 and 2-2 is a binding site to a neighboring atom.

In some embodiments, the photo acid generator may be at least one selected from Compounds 1 or 2:

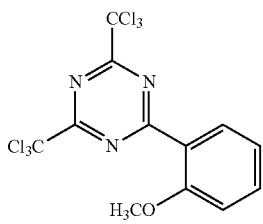

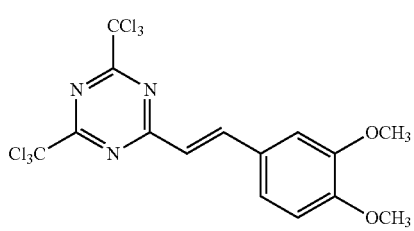

In some embodiments, the organic solvent may include propyleneglycol monomethyletheracetate.

In some embodiments, the photoresist composition may include the alkali soluble resin in an amount of about 5 wt. % to about 50 wt. %; the hardening agent in an amount of about 0.1 wt. % to about 15 wt. %; the photo acid generator in an amount of about 0.01 wt. % to about 10 wt. %; and the balance being the organic solvent.

Another embodiment provides a photoresist composition that includes an acryl copolymer in an amount of about 25 wt. %; a novolac-based resin in an amount of about 25 wt. %; a melamine-based resin in an amount of about 3 wt. % to about 7 wt. %; a photo acid generator represented by a Formula 1 in an amount of about 1 to about 7 wt %; and a balance being propylene glycol monomethyletheracetate. Formula 1 is

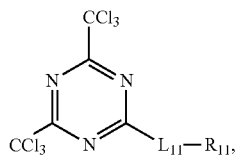

wherein $L_{11}$ is selected from a single bond, a $C_1$-$C_{10}$ alkylene group, a $C_2$-$C_{10}$ alkenylene group, and a $C_2$-$C_{10}$ alkynylene group; and $R_{11}$ is selected from a $C_6$-$C_{15}$ aryl group, or a $C_6$-$C_{15}$ aryl group with at least one substituent group selected from a group comprising deuterium, a hydroxyl group, a $C_1$-$C_{10}$ alkyl group, a $C_1$-$C_{10}$ alkoxy group, and a $C_6$-$C_{15}$ aryl group.

Another embodiment provides a method of manufacturing a substrate for a display device, wherein the method includes forming a photoresist layer on a substrate using a photoresist composition that includes a) an alkali soluble resin, b) a hardening agent, c) a photo acid generator represented by Formula 1, and d) an organic solvent; and exposing and developing the photoresist layer to form an organic insulating film having a first hole, <Formula 1>

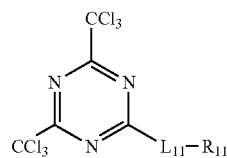

wherein in Formula 1, $L_{11}$ is selected from a single bond, a $C_1$-$C_{10}$ alkylene group, a $C_2$-$C_{10}$ alkenylene group, and a $C_2$-$C_{10}$ alkynylene group; and $R_{11}$ is selected from a $C_6$-$C_{15}$ aryl group, or a $C_6$-$C_{15}$ aryl group with at least one substitutent group selected from a group comprising deuterium, a hydroxyl group, a $C_1$-$C_{10}$ alkyl group, a $C_1$-$C_{10}$ alkoxy group, and a $C_6$-$C_{15}$ aryl group.

In some embodiments, exposing and developing the photoresist layer may include applying the photoresist composition on the substrate to form a coating film; irradiating light having a wavelength of about 400 nm to about 410 nm to the coating film, and developing an exposed coating film with a developer solution.

In some embodiments, irradiating light may be performed by irradiating a plurality of spot beams to the coating film using a digital exposure device, wherein the spot beams are selectively irradiated to exposed areas and are shielded from a contact hole formation area by turning on or off micromirrors of the digital exposure device, and a portion of the coating film on the contact hole formation area is removed using the developer solution.

In some embodiments, the method may further include, prior to the forming of the photoresist layer, forming a thin film transistor including a gate electrode, a source electrode, and a drain electrode, and a passivation layer on the substrate, wherein the photoresist layer is formed on the passivation layer.

In some embodiments, the method may further include, after exposing and developing the photoresist layer, etching the passivation layer using the organic insulating film having the first hole as an etch prevention film to form a second hole corresponding to the first hole, wherein the first and second holes define a contact hole that exposes a portion of the drain electrode; forming a transparent electrode layer on the organic insulating film with the first and second contact holes, and patterning the transparent electrode layer to form a pixel electrode, wherein the pixel electrode contacts the portion of the drain electrode through the first and second contact holes.

Other aspect and characteristics other than those described above will be obvious in view of the following drawings, claims, and detailed description of exemplary embodiments of the present disclosure.

BRIEF DESCRIPTION OF THE DRAWINGS

FIG. 2 shows SEM images of line-and-space patterns of Comparative Examples 1 and 2, and Example 1 to compare the resolutions and profiles thereof according to a pattern size.

DETAILED DESCRIPTION

Figure 1:
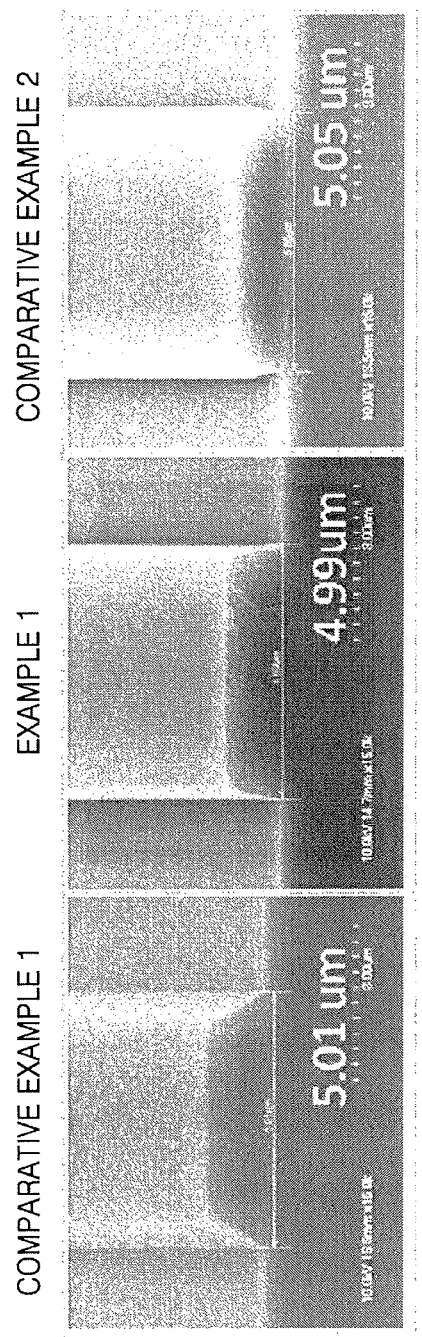
FIG. 1 shows scan electron microscope (SEM) images of 5 um line-and-space patterns of Comparative Examples 1 and 2 and Example 1 to compare the resolution and profile thereof.

Reference will now be made in detail to embodiments, examples of which are illustrated in the accompanying drawings, wherein like reference numerals may refer to the like elements throughout. In this regard, the present embodiments may have different forms and should not be construed as being limited to the descriptions set forth herein.

Hereinafter, structures and operations of embodiments of the inventive concept will be described in detail with reference to embodiments illustrated in the attached drawings, but embodiments of the inventive concept are not limited thereto. Herein, when an quantity is described as being about equal to another quantity, it is to be understood that the quantities are equal to each other, equal to within a measurement error, or different from each other but functionally the same as each other as would be understood by a person having ordinary skill in the art.

A photoresist composition according to an embodiment includes
an alkali soluble resin;
a hardening agent;
a photo acid generator represented by Formula 1; and
an organic solvent:

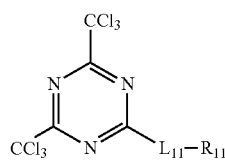

<Formula 1> wherein in Formula 1,
$L_{11}$ is selected from a single bond, a $C_1$-$C_{10}$ alkylene group, a $C_2$-$C_{10}$ alkenylene group, and a $C_2$-$C_{10}$ alkynylene group; and
$R_{11}$ is selected from a $C_6$-$C_{15}$ aryl group, or a $C_6$-$C_{15}$ aryl group with at least one substitution selected from a group comprising deuterium, a hydroxyl group, a $C_1$-$C_{10}$ alkyl group, a $C_1$-$C_{10}$ alkoxy group, and a $C_6$-$C_{15}$ aryl group.

(A) Alkali Soluble Resin

Examples of an alkali soluble resin are (A-1) an acryl copolymer and (A-2) a novolac-based resin.

(A-1) Acryl Copolymer

An acryl copolymer is alkali-soluble, and may be obtained by a radical polymerization reaction of an unsaturated carboxylic acid and an olefin-based unsaturated compound, which are monomers, in the presence of a solvent and a polymerization initiator.

When an amount of the acryl copolymer with respect to a total weight of the photoresist composition exceeds about 50 wt. %, at the same exposure amount, a residual film rate may be decreased, and when it is about 1 wt. % or lower, there may be no exfoliation improvement effects. Accordingly, an amount of the acryl copolymer may be in a range of about 1 wt. % to about 50 wt. % based on a total weight of the photoresist composition. For example, an amount of the acryl copolymer may be in a range of about 10 wt. % to about 25 wt. % based on a total weight of the negative photoresist composition.

Examples of an unsaturated carboxylic acid include a methacrylic acid and an acylic acid. These may be used alone or in combination. However, embodiments of the inventive concept are not limited thereto.

Examples of an olefin-based unsaturated compound include methylmethacrylate, ethylmethacrylate, n-butylmethacrylate, sec-butylmethacrylate, tert-butyl methacrylate, methylacrylate, isopropylacrylate, cyclohexyl methacrylate, 2-methylcyclohexylmethacrylate, dicyclopentanyloxyethylmethacrylate, isobonylmethacrylate, cyclohexyl acrylate, 2-methylcyclohexylacrylate, dicyclopentenylacrylate, dicyclopentanylacrylate, dicyclopentenylmethacrylate, dicyclopentanylmethacrylate, dicyclopentanyloxy ethylacrylate, isobonylacrylate, phenylmethacrylate, phenylacrylate, benzyl acrylate, benzyl methacrylate, 2-hydroxyethylmethacrylate, styrene, hydroxy styrene, α-methyl styrene, m-methyl styrene, p-methyl styrene, vinyltoluene, 1,3-butadiene, isoprene, and 2,3-dimethyl 1,3-butadiene. These may be used alone or in combination. However, embodiments of the inventive concept are not limited thereto.

The polymerization initiator may be a radical polymerization initiator. Examples of a polymerization initiator are 2,2'-azobisisobutyronitrile, 2,2'-azobis(2,4-dimethylvaleronitrile)), 2,2'-azobis(4-methoxy 2,4-dimethylvaleronitrile), 1,1'-azobis(a cyclohexane-1-carbonitrile), and dimethyl 2,2'-azobisisobutylate.

(A-2) Novolac-Based Resin

A novolac-based resin is alkali-soluble, and may be obtained by reacting a phenol-based compound with an aldehyde-based compound or a ketone-based compound in the presence of an acidic catalyst.

Examples of a phenol-based compound include phenol, ortho-cressol, meta-cresol, para-cresol, 2,3-dimethylphenol, 3,4-dimethylphenol, 3,5-dimethylphenol, 2,4-dimethylphenol, 2,6-dimethylphenol, 2,3,6-trimethylphenol, 2-t-butylphenol, 3-t-butylphenol, 4-t-butylphenol, 2-methylresorcinol, 4-methylresorcinol, 5-methylresorcinol, 4-t-butylcatechol, 2-methoxyphenol, 3-methoxyphenol, 2-propylphenol, 3-propylphenol, 4-propylphenol, 2-isopropylphenol, 2-methoxy-5-methylphenol, 2-t-butyl-5-methylphenol, thymol, and isothymol. These may be used alone or in combination. For example, a cresol novolac-based resin prepared by condensing formaldehyde and a mixture of about 75 wt. % of meta-cresol and about 25 wt. % of para-cresol, may be used in embodiments of the inventive concept. A weight average molecular weight of the novolac-based resin may be in a range of about 7,000 to about 30,000. In this regard, the weight average molecular weight is that of a monodispersed polystyrene measured by gel permeation chromatography (GPC). When the weight average molecular weight of the novolac-based resin is too low, even if a cross-linking reaction occurs in an exposed portion, a molecular weight increase effect may be too low and thus, the exposed portion may be easily dissolved in an alkali developing solution. When the weight average molecular weight of the novolac-based resin is too high, the difference in solubility of an exposed portion and a non-exposed portion with respect to the alkali developing solution may decrease, rendering it challenging to obtain an appropriate photolithography pattern.

The amount of a novolac-based resin may be in a range of about 5 wt. % to about 40 wt. % based on a total weight of the negative photoresist composition. For example, the amount of a novolac-based resin may be in a range of about 15 wt. % to about 25 wt. % based on a total weight of the negative photoresist composition.

Examples of an aldehyde-based compound include formaldehyde, formalin, paraformaldehyde, trioxane, acetaldehyde, propylaldehyde, benzaldehyde, phenylacetaldehyde, α-phenylpropylaldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-methylbenzaldehyde, m-methylbenzaldehyde, p-methylbenzaldehyde, p-ethylbenzaldehyde, p-n-butylbenzaldehyde, and terephthalic aldehyde. These may be used alone or in combination.

Examples of a ketone-based compound include acetone, methylethylketone, diethylketone, and diphenylketone. These may be used alone or in combination.

When the amount of an alkali soluble resin is in a range of about 25 wt. % to about 50 wt. % based on a total weight of the negative photoresist composition, a development margin, a residual film rate, a heat resistance property, and a photo sensitivity may be maximized. Accordingly, the amount of the alkali soluble resin may be in a range of about 25 wt. % to about 50 wt. % based on a total weight of the negative photoresist composition.

(B) Hardening Agent

The hardening agent may be combined with the alkali soluble resin to cross-link the alkali soluble resin. The hardening agent may be combined with the alkali soluble resin by heat.

Examples of a hardening agent include an epoxy-based resin, a polyglycidylether-based resin, a diphenyl ether-based resin, a styrene resin, and a melamine-based resin. However, embodiments of the inventive concept are not limited thereto.

An epoxy-based resin is a resin that has at least one epoxy group, and examples thereof include a conventional bisphenol A-type epoxy (diglycidyl ether of bisphenol A (DGEBA)) resin, a bisphenol F-type epoxy resin, a novolac-type epoxy resin, and a cycloaliphatic epoxy resin. Examples of a diphenyl ether-based resin include diphenyl ether, 1,3-diphenoxybenzene, and 1,2-diphenoxybenzene. Examples of a styrene resin include polyphenylethylene and polychlorotrifluoroethylene. Examples of a melamine-based resin include an alkoxymethylated melamine resin, an ethoxymethylated melamine resin, a propoxymethylated melamine resin, a butoxy methylated melamine resin, a hexamethoxymethylmelamine resin, a hexaethoxymethylmelamine resin, a hexabutoxymethylmelamine resin, and a hexaisobutoxymethylmelamine resin.

When the amount of a hardening agent is less than about 0.1 wt. % based on a total weight of the photoresist composition, the effect of the alkali soluble resin on the cross-linking decreases, and accordingly, even when an exposure process is performed and heat is provided, cross-linking may not not occur. When the amount of the hardening agent exceeds about 15 wt. % based on a total weight of the negative photoresist composition, the photoresist composition may be highly likely to be hardened when the temperature is raised. Thus, stability of the photoresist composition may decrease, rendering it challenging to preserve the photoresist composition. Accordingly, the amount of a hardening agent may be in a range of about 0.1 wt. % to about 15 wt. % based on a total weight of the photoresist composition. For example, the amount of a hardening agent may be in a range of about 3 wt. % to about 7 wt. % based on a total weight of the photoresist composition.

(C) Photo Acid Generator

A photo acid generator is a compound that generates an acid due to irradiation of an active light beam, and examples thereof include materials that generate a Bronsted acid or a Lewis acid. The acid generated by a photo acid generator may activate the hardening agent.

A photo acid generator may be represented by Formula 1 below:

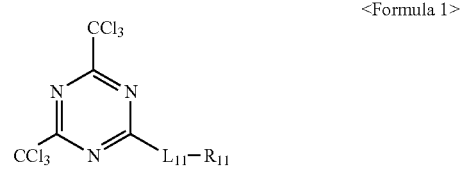

<Formula 1> wherein in Formula 1, $L_{11}$ is selected from a single bond, a $C_1$-$C_{10}$ alkylene group, a $C_2$-$C_{10}$ alkenylene group, and a $C_2$-$C_{10}$ alkynylene group;

$R_{11}$ is selected from a $C_6$-$C_{15}$ aryl group; or a $C_6$-$C_{15}$ aryl group with at least substitution selected from a group comprising deuterium, a hydroxyl group, a $C_1$-$C_{10}$ alkyl group, a $C_1$-$C_{10}$ alkoxy group, and a $C_6$-$C_{15}$ aryl group.

For example, $L_{11}$ in Formula 1 may be selected from a single bond and a $C_2$-$C_{10}$ alkenylene group, but embodiments are not limited thereto.

In some embodiments, $L_{11}$ in Formula 1 may be selected from a single bond and an ethenylene group, but embodiments are not limited thereto.

For example, $R_{11}$ in Formula 1 may be selected from a phenyl group, or a phenyl group with at least one substituent group selected from a methyl group, an ethyl group, an n-propyl group, an iso-propyl group, a methoxy group, an ethoxy group and a phenyl group, but embodiments are not limited thereto:

In some embodiments, $R_{11}$ in Formula 1 may be a phenyl group with a methoxy group, but embodiments are not limited thereto.

According to other embodiments, $R_{11}$ in Formula 1 may be selected from Formulae 2-1 to 2-2 below, but embodiments are not limited thereto:

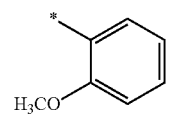

2-1

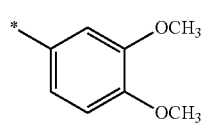

wherein * in Formulae 2-1 and 2-2 is a binding site to a neighboring atom.

According to other embodiments, the photo acid generator may be represented by Formula 1a:

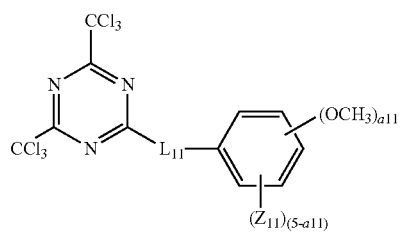

wherein in Formula 1a, $L_{11}$ is the same as that defined with respect to $L_{11}$ in Formula 1;

a11 is an integer of 1 or 2;

$Z_{11}$ is selected from hydrogen, a methyl group, an ethyl group, an n-propyl group, an iso-propyl group, a methoxy group, an ethoxy group, and a phenyl group.

The photo acid generator may be at least one selected from Compounds 1 and 2, below, but is not limited thereto:

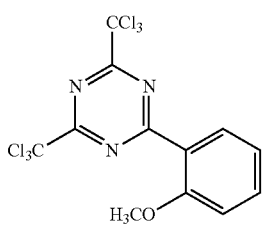

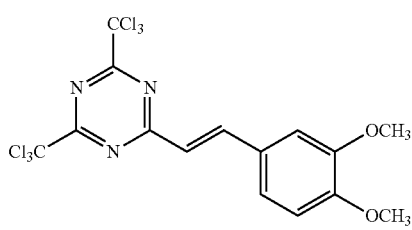

In a photo acid generator represented by Formula 1, $CCl_3$ in a triazine core in Formula 1' may decompose due to light, thereby producing HCl.

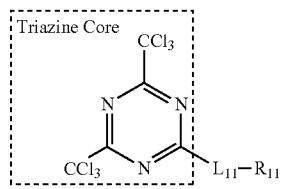

The amount of a photo acid generator may be in a range of about 0.01 wt. % to about 10 wt. % based on a total weight of the photoresist composition.

When the amount of a photo acid generator is less than about 0.01 wt. % based on a total weight of the photoresist composition, the amount of acid produced by the photo acid generator is negligible and thus, the photo acid generator may not contribute to the activation of the hardening agent. When the amount of the photo acid generator exceeds about 10 wt. % based on a total weight of the photoresist composition, even when a mask is disposed on a substrate with a film having the photoresist composition thereon and light is irradiated thereto, the photo acid generator may be highly likely to react to light. Thus, the subsequent development may perform slowly or improperly since a portion that should have been removed using the alkali developing solution may not have been removed. Accordingly, the amount of the photo acid generator may be in a range of about 0.01 wt. % to about 10 wt. % based on a total weight of the photoresist composition. In detail, the amount of the photo acid generator may be in a range of about 1 wt. % to about 7 wt. % based on a total weight of the photoresist composition.

(D) Organic Solvent

Examples of organic solvents include ethers, glycolethers, ethyleneglycol alkylether acetates, diethyleneglycols, propyleneglycol mono alkylethers, propyleneglycol alkyletheracetates, propyleneglycol alkyletheracetates, propyleneglycol monomethyletheracetates, aromatic hydrocarbons, ketones, and esthers.

For example, the organic solvent may be propyleneglycol monomethyletheracetate, but embodiments are not limited thereto.

For example, the photoresist composition may be a negative photoresist composition.

For example, the photoresist composition may include an alkali soluble resin in an amount of about 5 wt. % to about 50 wt. %; a hardening agent in an amount of about 0.1 wt. % to about 15 wt. %; a photo acid generator in an amount of about 0.01 wt. % to about 10 wt. %; and a balance of an organic solvent, but embodiments are not limited thereto.

In some embodiments, the photoresist composition may include an acryl copolymer in an amount of about 25 wt. %; a novolac-based resin in an amount of about 25 wt. %; a melamine-based resin in an amount of about 3 wt. % to about 7 wt. %; the photo acid generator represented by Formula 1 in an amount of about 3 to about 7 wt. %; with the balance being propylene glycolmonomethyletheracetate, but embodiments are not limited thereto.

Hereinafter, a method of manufacturing a substrate for a display device according to an embodiment will be described in related drawings.

Figure 7:
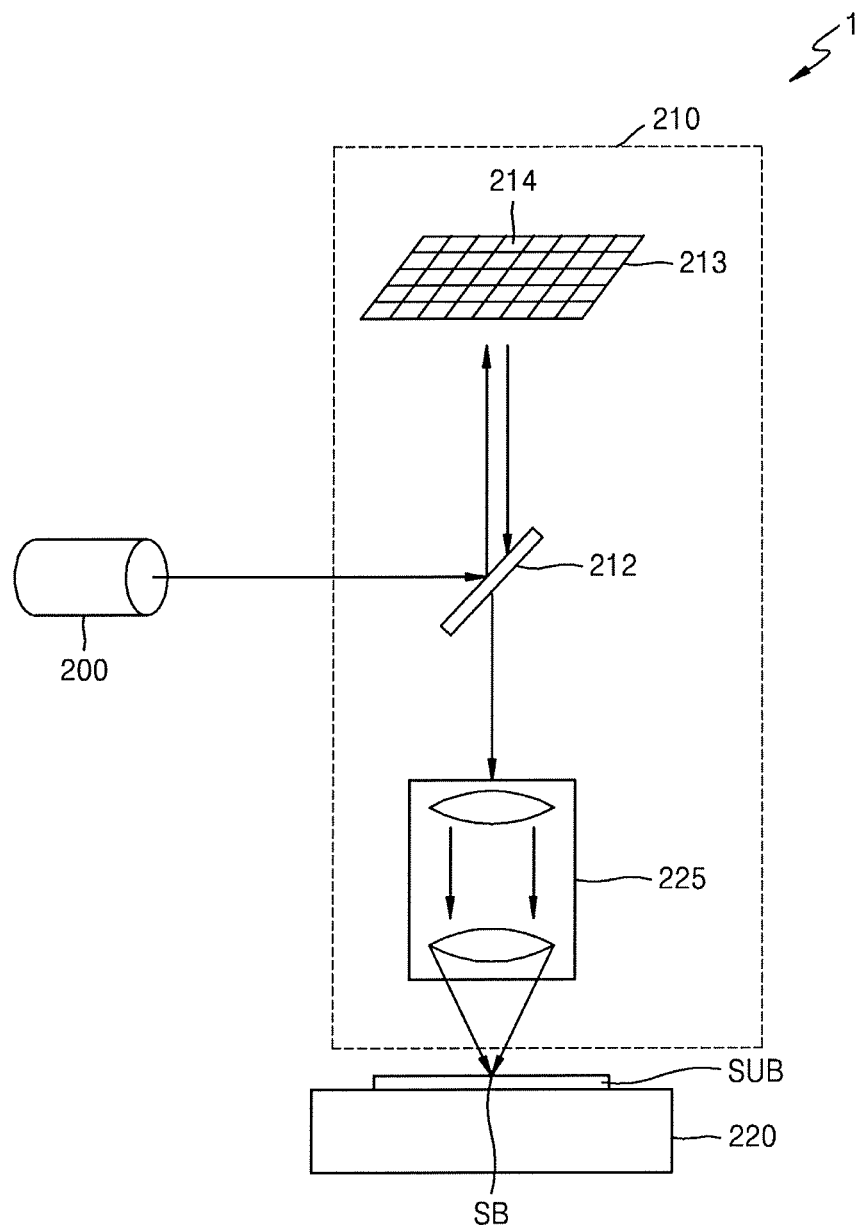
FIG. 7 illustrates a digital exposure device used to manufacture a substrate for a display device according to an embodiment.

FIG. 7 illustrates a digital exposure device 1 which is used to manufacture a substrate for a display device according to an embodiment.

Referring to FIG. 7, the digital exposure device 1 may include a light source 200 that can generate light, an optical head 210 that can receive light generated by the light source 200, and a stage 220 that can receive light from the optical head 210.

The light source 200 may emit a laser beam to the optical head 210.

The optical head 210 may include a beam splitter 212, a digital micro-mirror device 213, hereinafter referred to as DMD, and an optical system 225. In detail, the beam splitter 212 can reflect or transmit the laser beam received from the light source 200. The laser beam reflected by the beam splitter 212 is provided to the DMD 213. The beam splitter 212 transmits light received from the DMD 213 to the optical system 225.

The DMD 213 includes a plurality of micro-mirrors 214. The micro-mirrors 214 may be arranged in an m×n matrix form. Each of the micro-mirrors 214 may reflect light received from the beam splitter 212. The DMD 213 may selectively reflect the light received from the beam splitter 212 based on image data that is to be transferred onto a substrate SUB placed on the stage 220. The optical head 210 may further include a mirror controller that can control the micro-mirrors 214 based on the image data. The mirror controller may output a signal to turn the micro-mirrors 214 on or off. When the micro-mirrors 214 receives data from the mirror controller that indicate that all micro-mirrors are turned on, the number of reflection beams output to the optical system 225 may be substantially the same as the number of micro-mirrors 214

The optical system 225 includes a plurality of lenses. The optical system 225 may convert the reflection beams received from the DMD 213 into a plurality of spot beams SB. The optical system 225 may focus the reflection beams received from the DMD 213, and may enlarge intervals between the reflection beams.

Figure 9:
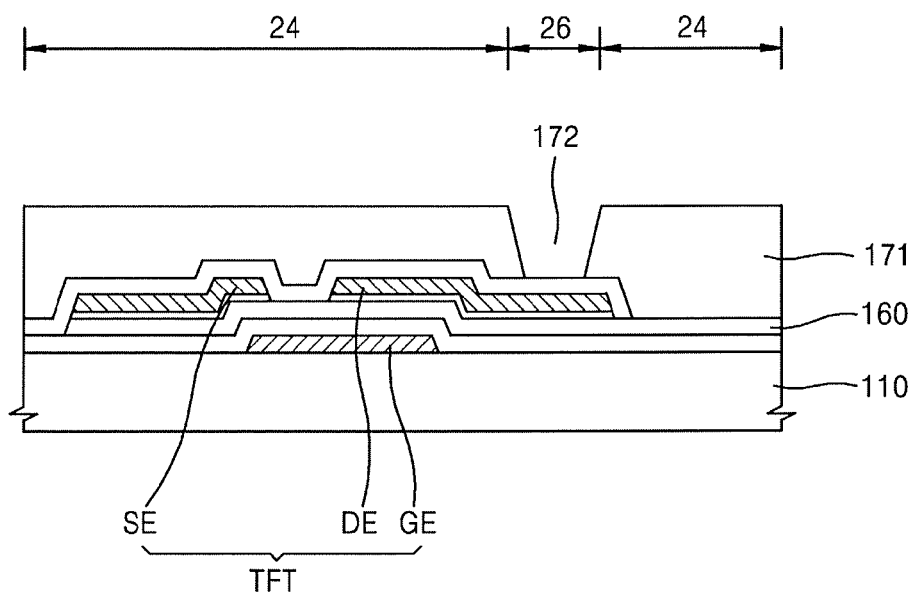
FIGS. 9 and 10 are cross-sectional views of a display device that illustrate a substrate for a display device according to an embodiment.
Figure 10:
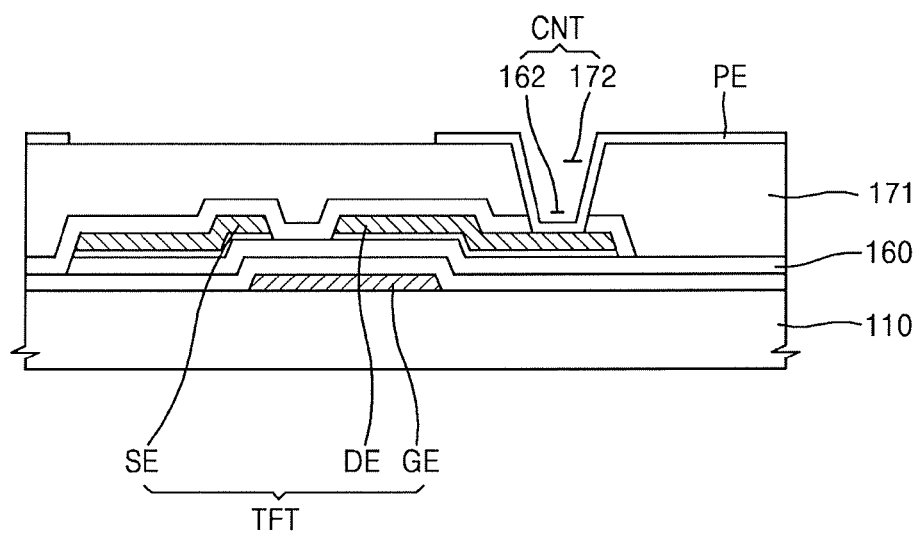

In the digital exposure device 1, the spot beams SB are irradiated to the substrate SUB placed on the stage 220 to expose a photoresist layer formed on the substrate SUB. Hereinafter, the substrate SUB will be described as being substantially the same as a base substrate 110 on which a passivation layer 160 with coating film thereon is formed, as shown in FIGS. 9 and 10.

Figure 8:
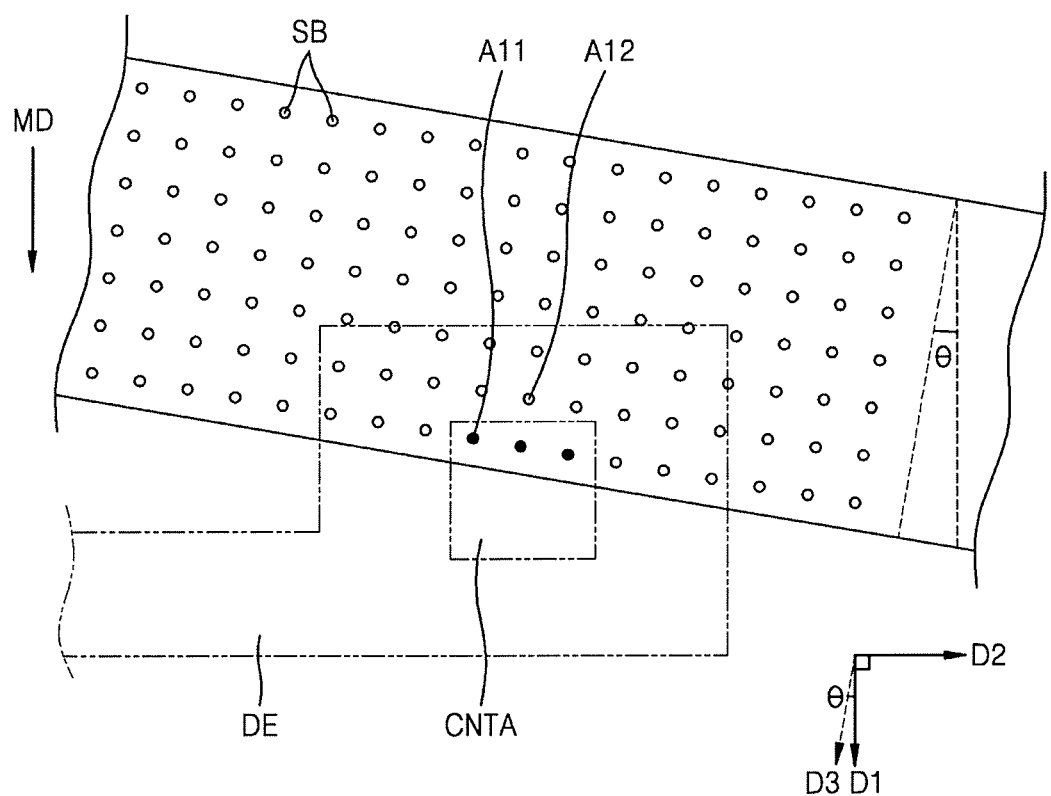
FIG. 8 is a plan view of a digital exposure device that illustrates an exposure process performed using a digital exposure device illustrated in FIG. 7.

FIG. 8 is a plan view of a digital exposure device that illustrates an exposure process performed using the digital exposure device 1 illustrated in FIG. 7.

Referring to FIGS. 7 and 8, the substrate SUB may be exposed by the spot beams SB.

In detail, let the DMD 213 be fixed at an inclination angle θ with respect to the substrate SUB to expose a continuous line or area in a second direction D2 perpendicular to a first direction D1, which is a scan direction MD. Accordingly, the substrate SUB is disposed with respect to the DMD 213 at the angle θ in a third direction D3. When the DMD 213 is fixed at a particular position, as the substrate SUB moves in the scan direction MD, the spot beams SB irradiate overlapping areas of the substrate SUB. The spot beams SB may be selectively transmitted to the substrate SUB according to whether the micro-mirrors 214 are turned on or off.

In some embodiments, some micro-mirrors corresponding to non-exposed areas receive off-data, and other micro-mirrors corresponding to an exposed area receive on-data. When a micro-mirror 214 receives off-data, no spot beam is transmitted to the substrate SUB. When a micro-mirror 214 receives on-data, a spot beam SB is transmitted to the substrate SUB. For ease of explanation, when a micro-mirror 214 receives off-data and thus is disposed above a non-exposed area, a corresponding spot is indicated as "●" and referred to as a "shielded spot." Also, when a micro-mirror 214 receives on-data and thus is disposed above an exposed area, a corresponding spot is indicated as "○" and referred to as an "exposed spot."

To form holes in a contact hole formation area CNTA, the contact hole formation area CNTA is determined to be a non-exposed area, and the remaining areas other than the contact hole formation area CNTA are determined to be exposed areas, and corresponding on/off-data is transmitted to the micro-mirrors 214.

When a micro-mirror is disposed over the contact hole formation area CNTA, the micro-mirror receives off-data to define a shielded spot A11 in the substrate SUB. A micro-mirror that is disposed over the remaining area receives on-data and provides a spot beam SB to the substrate SUB to define an exposure spot A12 in the substrate SUB. When the substrate SUB moves in the scan direction MD, the micro-mirror that has defined the exposure spot A12 in the remaining area in the previous step is now disposed over the contact hole formation area CNTA. Accordingly, the micro-mirror that has defined the exposure spot A12 in the previous step receives off-data to define a shielded spot in the substrate SUB in a current step.

Through these steps, the contact hole formation area CNTA does not receive the spot beams SB and the remaining area receives the spot beams SB. By developing a coating film that has been exposed by the digital exposure device, a hole may be formed in the contact hole formation area CNTA.

FIGS. 9 and 10 are cross-sectional views that illustrate a substrate for a display device according to an embodiment.

Referring to FIG. 9, a thin film transistor TFT that includes a gate electrode GE, a source electrode SE, and a drain electrode DE, and the passivation layer 160 may be formed on the base substrate 110.

A coating film may be formed on the passivation layer 160 using a photoresist composition according to an embodiment, and the coating film is exposed and developed to form an organic insulating film 171 having a first hole 172. The photoresist composition may be the same as described above.

The coating film may be exposed using the digital exposure device 1 illustrated in FIG. 7. Light having a wavelength of about 400 nm to about 410 nm may irradiate the coating film. To perform an exposing process using a digital exposure device, such as device 1 of FIG. 7, the base substrate 110 may be divided into an exposed area 24 and a shielded area 26. If an exposure amount with respect to the exposed area 24 is represented as "1", an exposure amount with respect to the shielded area 26 may be 0. The exposure amounts of the exposed area 24 and the shielded area 26 may be determined by controlling on/off-data of the micro-mirrors 214 of a digital exposure device, such as device 1 of FIG. 7.

After development, a portion of the coating film corresponding to the exposed area 24 may retain its original thickness. However, a portion of the coating film corresponding to the shielded area 26 may be removed using a developing solution, thereby leaving the first hole 172 therein.

Then, referring to FIG. 10, the passivation layer 160 may be etched using the organic insulating film 171 having the first hole 172 as an etch prevention film to form a second hole 162 corresponding to the first hole 172. The first and second holes 172 and 162 may be defined as a contact hole CNT that exposes a portion of the drain electrode DE.

Then, on the organic insulating film 170 with the contact hole CNT thereon, a transparent electrode layer may be formed, and the transparent electrode layer may be patterned to form a pixel electrode PE. The pixel electrode PE may include indium oxide. In detail, the pixel electrode PE may include indium tin oxide (ITO) or indium zinc oxide (IZO). The pixel electrode PE may directly contact the drain electrode DE through the contact hole CNT. Since the organic insulating film 170 is formed using a photoresist composition according to an embodiment, the pixel electrode PE may be stably formed on the organic insulating film 170.

As described above, since the organic insulating film 170 is formed using a photoresist composition according to an embodiment, even if light having a wavelength of about 405 nm is provided to the photoresist composition in an exposure process, due to the high photo sensitivity of the photoresist composition with respect to the light, the organic insulating film 170 may be easily formed. Also, the photoresist composition may increase an adhesive force between the organic insulating film 170 and the pixel electrode PE.

The high photo sensitivity of the photoresist composition with respect to light may also help stabilize a profile of a different thickness portions of a photo pattern. The increased formation reliability of the photo pattern 150 may also improve the manufacturing reliability of the source electrode SE and the drain electrode DE.

In some embodiments, the photoresist composition may be used to form a photo pattern to form a gate pattern. In some embodiments, the photoresist composition may be used to pattern the transparent electrode layer to form the pixel electrode PE.

Hereinafter, referring to FIGS. 1-6, a photoresist composition according to embodiments will be described in detail with reference to detailed examples and comparative examples. However, these examples are exemplary and non-limiting, and embodiments of the inventive concept are no limited thereto.

EXAMPLE 1

A photoresist composition that includes 25 wt. % of novolac resin including 75 wt. % of meta-cresol and 25 wt. % of para-cresol, 8 wt. % of acryl copolymer, 1 wt. % of Compound 2, 7 wt. % of hexamethoxymethylmelamine, and the balance being propylene glycolmonomethyletheracetate, was prepared.

COMPARATIVE EXAMPLE 1

Meta-cresol and para-cresol were mixed at a weight ratio of about 60:40, formaline was added thereto, and then, a condensation process was performed on the result using an oxalic acid catalyst according to a conventional method to prepare a cresol novolac-based resin. The cresol novolac-based resin was subjected to a fractionation process, and cut to remove a polymer area and a low molecular weight such that a weight average molecular weight of the novolac-based resin was 15,000.

COMPARATIVE EXAMPLE 2

A photoresist composition was prepared in the same manner as in Example 1, except that an amine-based resin was used instead of the novolac resin.

<Photolithography Pattern Characteristics Evaluation>

Each of the photoresist compositions prepared according to Example 1, Comparative Example 1 and Comparative Example 2 was spin coated on a hexamethyldisilazane (HDMS)-coated silicon wafer substrate to form a photoresist film having a thickness of about 1.3 um. Then, the photoresist films were soft baked at a temperature of about 105 degrees Celsius for about 90 seconds. Then, an exposure process was performed on the substrate using a digital exposure device that includes a plurality of micro-mirrors, and then the substrate was post-exposure baked (PEB). The post-exposure baking process was performed at a temperature of about 105 degrees Celsius for about 120 seconds. Then, the substrate was developed using an aqueous solution of 2.38 wt. % tetramethyl ammonium hydroxide (TMAH) at a temperature of about 23 degrees Celsius for about 60 seconds to form a photolithography pattern. Then, the profile, resolution, pattern shape, focus margin, and heat-resistance of the photolithography pattern were evaluated.

<Profile and Resolution>

A resolution refers to a minimum separation line width of a line-and-space pattern when an exposure process is performed with an effective degree of sensitivity, i.e., an exposure amount when a cross-section of a line-and-space pattern is 1:1.

A pattern angle refers to an angle between a substrate and a side wall of the photolithography pattern in a scan electron microscopic (SEM) image of a photolithography pattern.

FIG. 1 shows SEM images of 5 um line-and-space patterns of Comparative Examples 1 and 2 and Example 1 to compare the resolution and profile thereof.

Referring to FIG. 1, for Comparative Example 1, the resolution was 5.01 um, and a cross-section of the line pattern was relatively narrower upwards from a surface of the substrate, having a trapezoid shape. The angle between the line pattern and the substrate was about 47 degrees.

For Comparative Example 2, the resolution was 5.05 um, and a taper angle of the line pattern was about 103 degrees. That is, the line pattern had a reverse-taper shape. Regarding Comparative Example 2, a reverse-taper shape and a undercut shape were formed.

For Example 1, the resolution was 4.99 um, and the cross-section of the line pattern was rectangular. The angle between the line pattern and the substrate was about 75 degrees. Since the line pattern is maintained at 90 degrees or less, Example 1 may have excellent processability. Also, the line pattern did not have an undercut shape.

FIG. 2 shows SEM images of line-and-space patterns of Comparative Examples 1 and 2, and Example 1 to compare the resolutions and profiles thereof according to a pattern size.

Referring to FIG. 2, for Comparative Example 1, with respect to a 3 um line-and-space pattern, the resolution was 2.99 um, and the line pattern had a trapezoidal cross-section. It was confirmed that as the width of the line-and-space pattern decreases, the cross-section of the line pattern changes from the trapezoidal shape to a triangular shape.

In the case of Comparative Example 2, with respect to a 3 um line-and-space pattern, the resolution was 3.76 um, and for a line-and-space pattern smaller than the 3 um line-and-space pattern, the resolution was not measurable. With respect to a 1.8 um and a 1.6 um line-and-space pattern, no line patterns could be obtained.

In the case of Example 1, even when the size of a line-and-space pattern decreased, a line pattern having a rectangular cross-section was obtained, showing excellent processability. Also, the line patterns did not have a reverse-taper or undercut shape. As shown in the line patterns of FIG. 2, the use of a photoresist composition according to embodiments results in a high resolution pattern.

<Focus Margin>

When an exposure process is performed on a photoresist composition while changing the focus of an exposure device, a focus margin is identifiable using a formed photolithography pattern.

Figure 3:
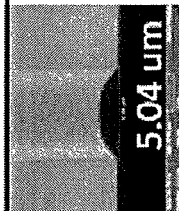
FIG. 3 shows SEM images of 5 um line-and-space patterns of Comparative Examples 1 and 2 and Example 1 to compare focus margins when a focus of an exposure device varies.
Figure 4:
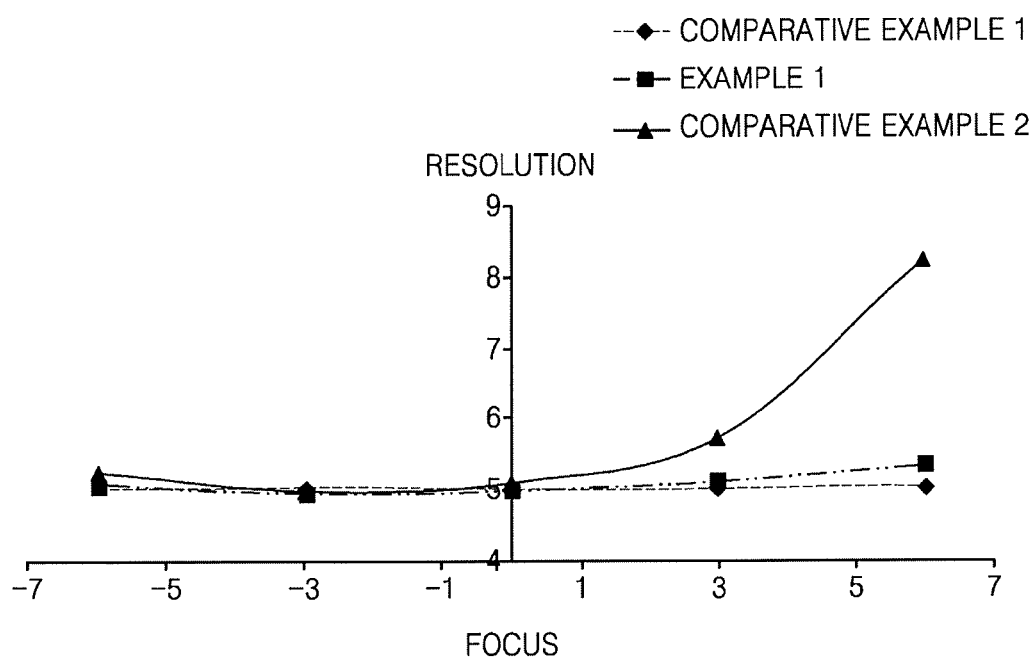
FIG. 4 shows a graph of resolution of the focus margin of Comparative Examples 1 and 2, and Example 1 illustrated in FIG. 3.

FIG. 3 shows SEM images of 5 um line-and-space patterns of Comparative Examples 1 and 2 and Example 1 to compare focus margins when a focus of the exposure device varies, and FIG. 4 shows a graph of resolution of the focus margin of Comparative Examples 1 and 2, and Example 1 illustrated in FIG. 3.

Referring to FIGS. 3 and 4, for Comparative Example 1, when the focus is less than −9 and greater than +6, the side wall of a photolithography pattern collapses.

For Comparative Example 2, when the focus was −9, the size of the photolithography pattern was about 34% greater than 5 um, and the side wall of the photolithography pattern collapsed. When the focus increased, for example, to +6, the side wall of the photolithography pattern collapsed and the width of the photolithography pattern was 165% greater than 5 um.

For Example 1, even when the focus changed from −9 to +6, the profile of the photolithography pattern did not change. Since Example 1 allows an exposure device to have a greater focus margin, a photolithography pattern with improved resolution may be formed.

<Heat-Resistance>

The heat resistance was evaluated such that photolithography patterns which had been developed were hard baked at different temperatures, and then SEM images of the photolithography patterns were obtained to identify flowability of the photolithography patterns.

Figure 5:
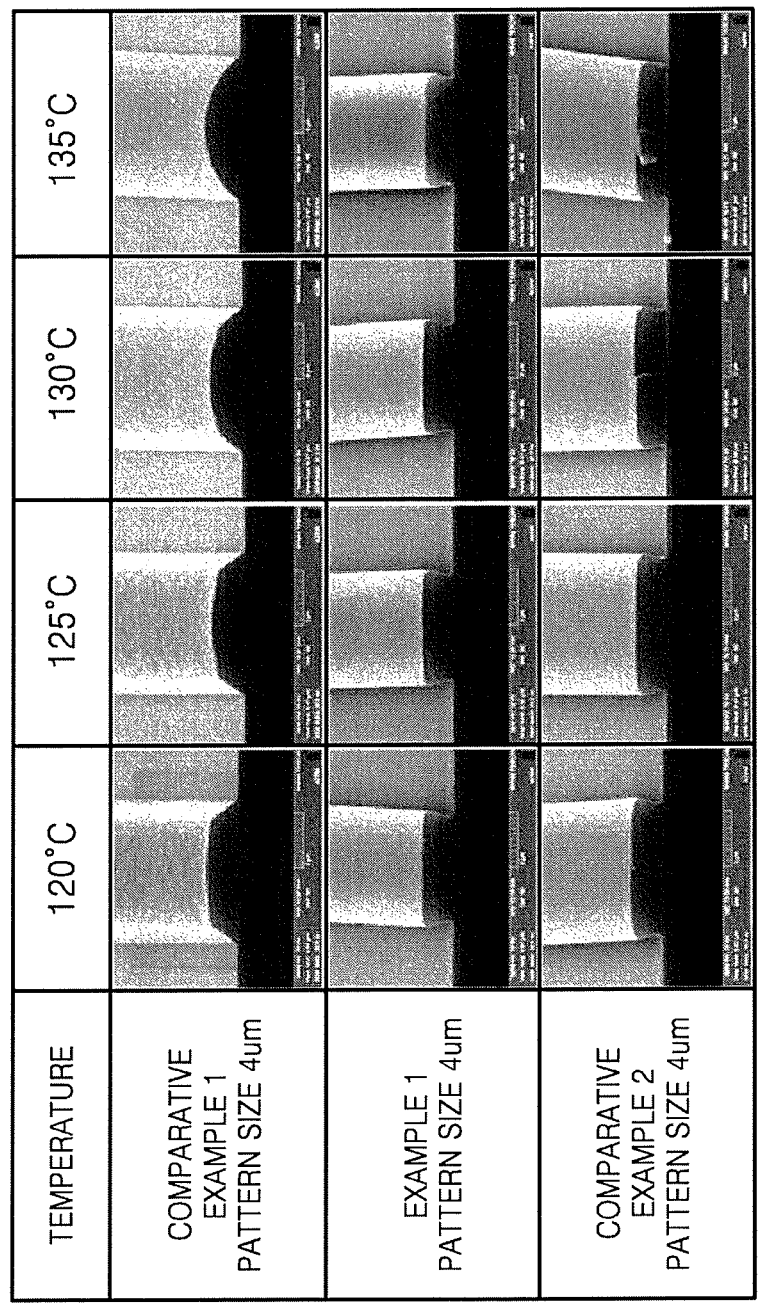
FIG. 5 shows SEM images of 4 um line-and-space patterns of Comparative Examples 1 and 2 and Example 1 to compare heat resistance at different hard-bake temperatures.

FIG. 5 shows SEM images of 4 um line-and-space patterns of Comparative Examples 1 and 2 and Example 1 to compare heat resistance at different hard-bake temperatures.

Referring to FIG. 5, for Comparative Example 1, as the hard bake temperature increased, reflow of the photolithography pattern more strongly occurred. At a temperature of about 135 degrees Celsius or higher, the side wall of the photolithography pattern collapsed.

For Comparative Example 2, when the hard bake temperature increased, the profile of the photolithography pattern did not change.

In the case of Example 1, even when the hard bake temperature increased, the profile of the photolithography pattern did not change. That is, the photoresist composition of Example 1 showed excellent heat resistance.

Figure 6:
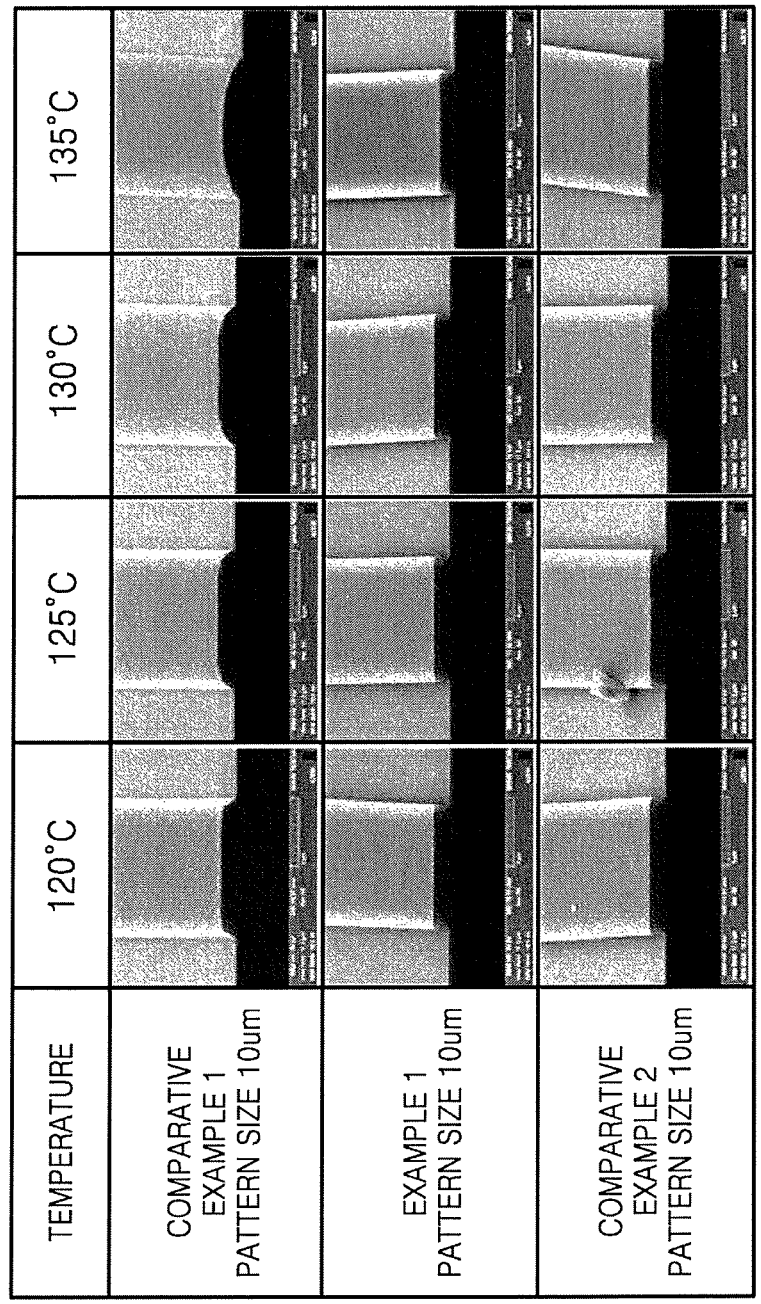
FIG. 6 shows SEM images of 10 um line-and-space patterns of Comparative Examples 1 and 2 and Example 1 to compare heat resistance at different hard-bake temperatures.

FIG. 6 shows SEM images of 10 um line-and-space patterns of Comparative Examples 1 and 2 and Example 1 to compare heat resistance at different hard-bake temperatures.

Referring to FIG. 6, for Comparative Example 1, as the hard bake temperature increased, reflow of the photolithography pattern more strongly occurred. At a temperature of about 130 degrees Celsius or higher, the side wall of the photolithography pattern collapsed.

For Comparative Example 2, when the hard bake temperature increased, the profile of the photolithography pattern did not change.

For Example 1, even when the hard bake temperature increased, the profile of the photolithography pattern did not change. That is, the photoresist composition of Example 1 showed excellent heat resistance.

A photoresist composition according to embodiments may have improved light characteristics. A method of manufacturing a display substrate using a photoresist composition according to embodiments may improve manufacturing reliability.

It should be understood that exemplary embodiments as described herein should be considered as descriptive only and not for purposes of limitation. Descriptions of features or aspects within each embodiment should typically be considered as available for other similar features or aspects in other embodiments.

What is claimed is:

1. A photoresist composition, comprising
   an acryl copolymer in an amount of 25 wt. %;
   novolac-based resin in an amount of 25 wt. % comprising a mixture of 75 wt. % of meta-cresol and 25 wt. % of para-cresol;
   a melamine-based resin in an amount of about 3 wt. % to about 7 wt. %;
   a photo acid generator represented by a Formula 1 in an amount of about 1 to about 7 wt. %; and
   a balance being propylene glyeolmonomethyletheracetate, <Formula 1>

[Chemical structure: triazine ring with two CCl₃ groups and an $L_{11}-R_{11}$ group]

wherein in Formula 1,
$L_{11}$ is selected from a single bond a $C_1$-$C_{10}$ alkylene group, a $C_2$-$C_{10}$ alkenylene group, and a $C_2$-$C_{10}$ alkynylene group; and
$R_{11}$ is selected from a $C_6$-$C_{15}$ aryl group, or a $C_6$-$C_{15}$ aryl group with at least one substitutent group selected from a group comprising deuterium, a hydroxyl group, a $C_1$-$C_{10}$ alkyl group, a $C_1$-$C_{10}$ alkoxy group, and a $C_6$-$C_{15}$ aryl group.

2. The photoresist composition of claim 1, wherein
the novolac-based resin has a weight average molecular weight of about 7,000 to about 30,000, based on polystyrene.

3. The photoresist composition of claim 1, wherein
$L_{11}$ is selected from a single bond and a $C_2$-$C_{10}$ alkenylene group.

4. The photoresist composition of claim 1, wherein
$L_{11}$ is selected from a single bond and an ethenylene group.

5. The photoresist composition of claim 1, wherein
$R_{11}$ is a phenyl group; or
a phenyl group with at least one substitutent group selected from a methyl group, an ethyl group, an n-propyl group, an iso-propyl group, a methoxy group, an ethoxy group and a phenyl group.

6. The photoresist composition of claim 1, wherein
$R_{11}$ is a phenyl group with a methoxy group.

7. The photoresist composition of claim 1, wherein
$R_{11}$ is selected from Formulae 2-1 or 2-2:

2-1

[Chemical structure: phenyl group with methoxy (H₃CO) substituent]

-continued

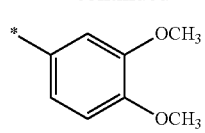

2-2 in Formulae 2-1 and 2-2,
wherein * indicates a binding site to a neighboring atom.

8. The photoresist composition of claim 1, wherein the photo acid generator comprises at least one selected from Compounds 1 or 2:

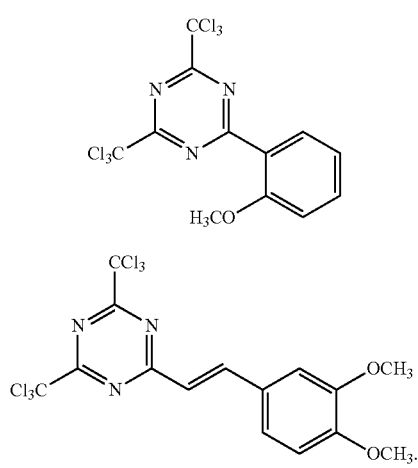

9. A method of manufacturing a substrate for a display device, the method comprising:
forming a photoresist layer on a substrate using a photoresist composition that includes a) an alkali soluble resin, b) a hardening agent, e) a photo acid generator represented by Formula 1, and d) an organic solvent; and
exposing and developing the photoresist layer to form an organic insulating film having a first hole, <Formula 1>

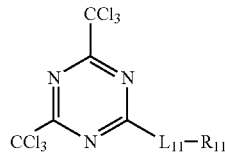

wherein in Formula 1,
$L_{11}$ is selected from a single bond, a $C_1$-$C_{10}$ alkylene group, a $C_2$-$C_{10}$ alkenylene group, and a $C_2$-$C_{10}$ alkynylene group; and
$R_{11}$ is selected from a $C_6$-$C_{15}$ aryl group; or
a $C_6$-$C_{15}$ aryl group with at least one substitutent group selected from a group comprising deuterium, a hydroxyl group, a $C_1$-$C_{10}$ alkyl group, a $C_1$-$C_{10}$ alkoxy group, and a $C_6$-$C_{15}$ aryl group.

10. The method of claim 9, wherein exposing and developing the photoresist layer comprises
applying the photoresist composition on the substrate to form a coating film irradiating light having a wavelength of about 400 nm to about 410 nm to the coating film; and
developing the coating film with a developer solution.

11. The method of claim 10, wherein irradiating light comprises
irradiating a plurality of spot beams to the coating film using a digital exposure device,
wherein the spot beams are selectively irradiated to exposed areas and are shielded from a contact hole formation area by turning on or off micro-mirrors of the digital exposure device, and a portion of the coating film on the contact hole formation area is removed using the developer solution.

12. The method of claim 9, further comprising
prior to the forming of the photoresist layer, forming a thin film transistor comprising a gate electrode, a source electrode, and a drain electrode, and a passivation layer on the substrate, wherein the photoresist layer is formed on the passivation layer.

13. The method of claim 12, further comprising
after exposing and developing the photoresist layer, etching the passivation layer using the organic insulating film having the first hole as an etch prevention film to form a second hole corresponding to the first hole, wherein the first and second holes define a contact hole that exposes a portion of the drain electrode;
forming a transparent electrode layer on the organic insulating film with the first and second contact holes, and
patterning the transparent electrode layer to form a pixel electrode, wherein the pixel electrode contacts the portion of the drain electrode through the first and second contact holes.

14. A photoresist composition comprising:
an acryi copolymer in an amount of 25 wt. %;
a novolac based resin in an amount of 25 wt. %;
a melamine-based resin in an amount of about 3 wt. % to about 7 wt. %;
a photo acid generator comprising at least one selected from Compounds 1 and 2 in an amount of about 1 to about 7 wt. %; and
a balance being propylene glyeolmonomethyletheracetate,

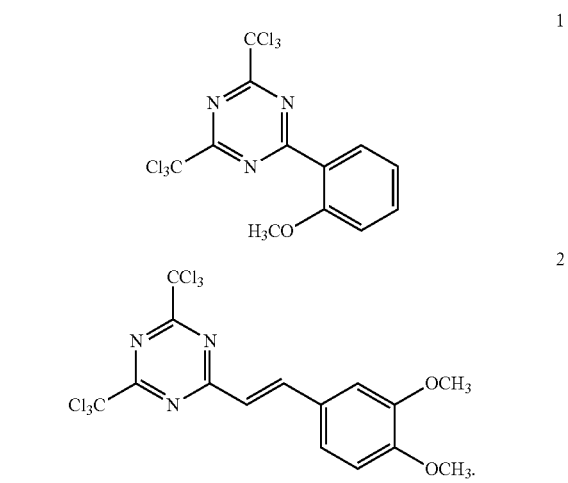

15. The photoresist composition of claim 14, wherein the novolac-based resin comprises a mixture of 75 wt. % of meta-cresol and 25 wt. % of para-cresol.

16. The photoresist composition of claim 14, wherein the novolac-based resin has a weight average molecular weight of about 7,000 to about 30,000, based on polystyrene.

\* \* \* \* \*